(12) United States Patent
Kuiken

(10) Patent No.: US 7,044,984 B2
(45) Date of Patent: May 16, 2006

(54) HIGH PROFILE MULTIAXIAL PROSTHETIC FOOT

(75) Inventor: Todd A. Kuiken, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 09/558,570

(22) Filed: Apr. 26, 2000

(65) Prior Publication Data

US 2002/0143407 A1   Oct. 3, 2002

(51) Int. Cl.
*A61F 2/66* (2006.01)
*A61F 2/64* (2006.01)

(52) U.S. Cl. .......................................... 623/55; 623/47
(58) Field of Classification Search ............. 623/47–56
See application file for complete search history.

(56) References Cited

U.S. PATENT DOCUMENTS

| | | | | |
|---|---|---|---|---|
| 1,334,861 A | * | 3/1920 | Ingebrigtsen | 623/55 |
| 2,692,990 A | * | 11/1954 | Schaefer | 623/55 |
| 4,547,913 A | | 10/1985 | Phillips | 623/27 |
| 4,822,363 A | | 4/1989 | Phillips | 623/27 |
| 4,959,073 A | | 9/1990 | Merlette | 623/55 |
| 4,994,086 A | | 2/1991 | Edwards | 623/26 |
| 5,116,383 A | * | 5/1992 | Shorter et al. | 623/49 |
| 5,116,384 A | * | 5/1992 | Wilson et al. | 623/49 |
| 5,116,385 A | | 5/1992 | Allard et al. | 623/55 |
| 5,156,631 A | | 10/1992 | Merlette | 623/52 |
| 5,181,933 A | | 1/1993 | Phillips | 623/55 |
| 5,201,775 A | | 4/1993 | Arbogast et al. | 623/38 |
| 5,217,500 A | | 6/1993 | Phillips | 623/38 |
| 5,314,499 A | | 5/1994 | Collier | 623/47 |
| 5,376,141 A | | 12/1994 | Phillips | 623/55 |
| 5,443,527 A | | 8/1995 | Wilson | |
| 5,486,209 A | | 1/1996 | Phillips | 623/52 |
| 5,514,185 A | | 5/1996 | Phillips | 623/52 |
| 5,571,212 A | | 11/1996 | Cornelius | |
| 5,593,456 A | | 1/1997 | Merlette | 623/49 |
| 5,593,457 A | | 1/1997 | Phillips | 623/52 |
| 5,728,176 A | | 3/1998 | Phillips | 623/52 |
| 5,766,265 A | | 6/1998 | Phillips | 623/52 |
| 5,776,205 A | | 7/1998 | Phillips | 623/55 |
| 5,800,568 A | * | 9/1998 | Atkinson et al. | 623/52 |
| 5,824,112 A | | 10/1998 | Phillips | 623/52 |
| 6,053,946 A | * | 4/2000 | Wilkinson | 623/52 |
| 6,206,934 B1 | * | 3/2001 | Phillips | 623/53 |
| 6,228,124 B1 | * | 5/2001 | Slemker et al. | 623/47 |
| 6,261,324 B1 | * | 7/2001 | Merlette | 623/55 |

FOREIGN PATENT DOCUMENTS

FR    2 653 327 A1   4/1991
GB      518 258 A    2/1940

* cited by examiner

*Primary Examiner*—Bruce E. Snow
(74) *Attorney, Agent, or Firm*—Gardner Carton & Douglas LLP

(57) ABSTRACT

The present invention provides a prosthetic foot that provides both energy storage capabilities and stability. The prosthetic foot of the present invention provides medial-lateral rotation as compared to the slight tilting or rocking in the medial-lateral plane of the prior art devices. Furthermore, the prosthetic foot of the present invention provides a true hinge in the ankle joint region that may be adapted so that the degree of rotation is controlled.

6 Claims, 4 Drawing Sheets

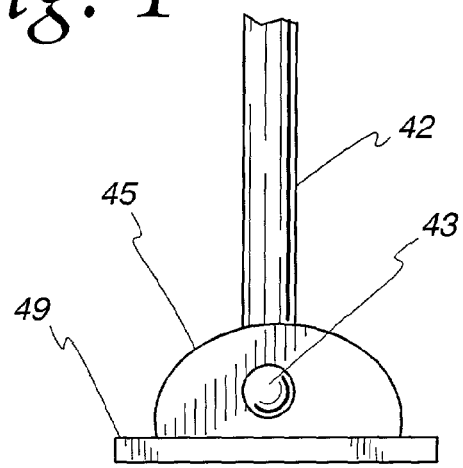
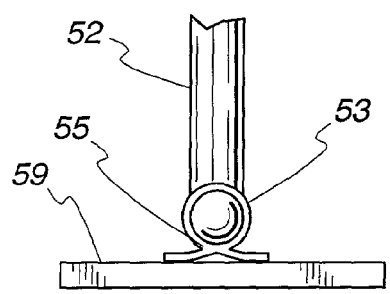
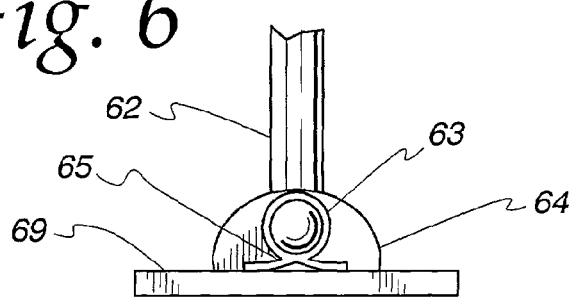
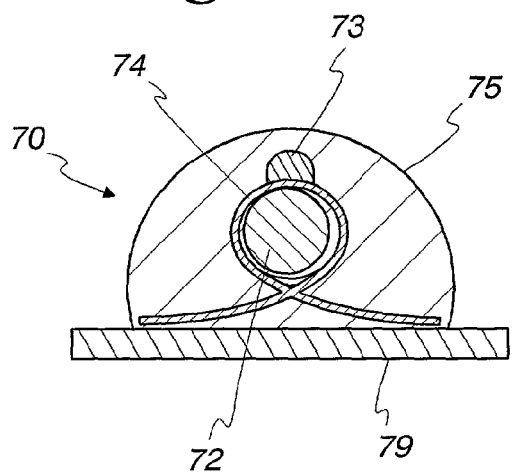
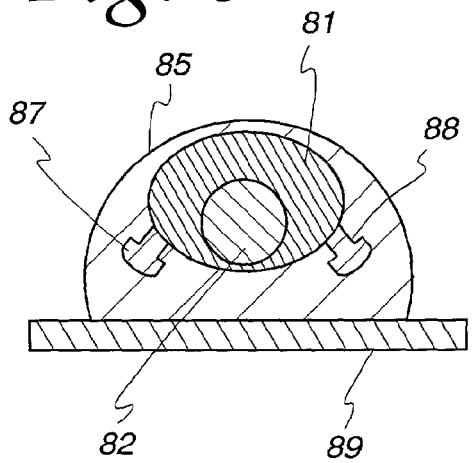

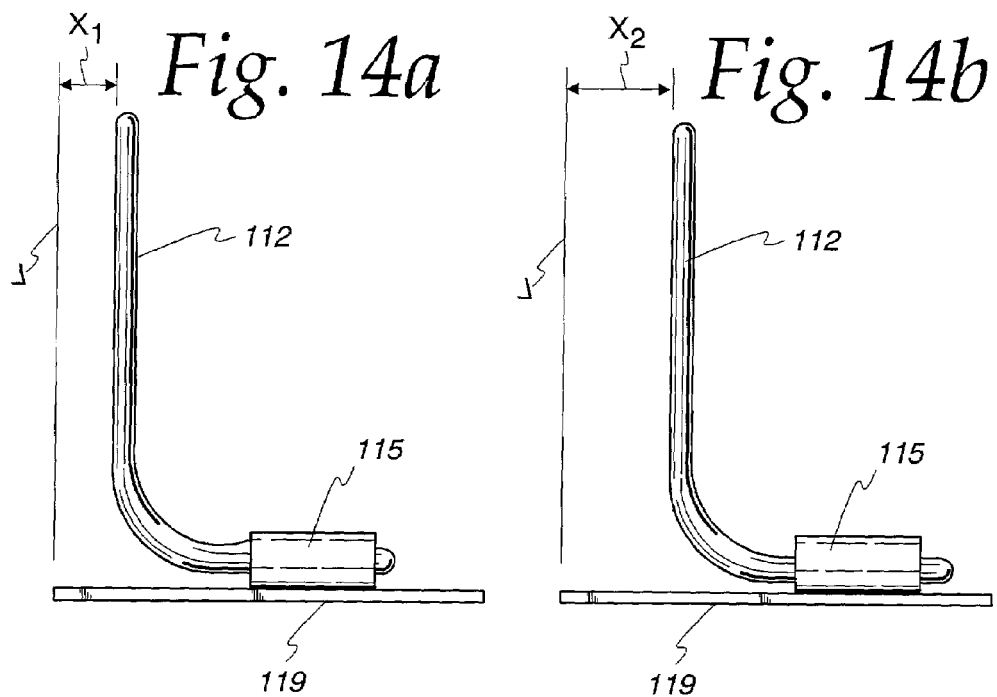
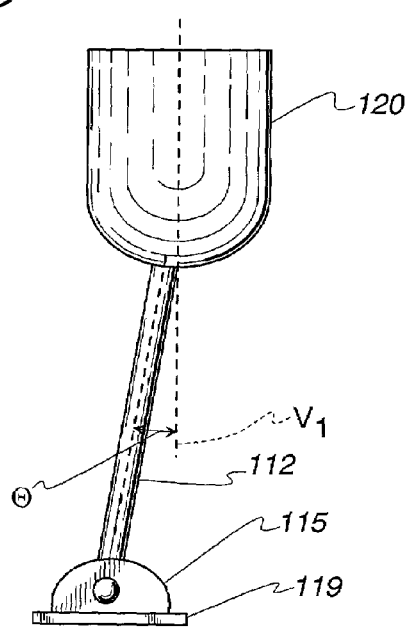

HIGH PROFILE MULTIAXIAL PROSTHETIC FOOT

FIELD OF THE INVENTION

The present invention relates to a high-profile prosthetic foot that provides up to 180° of medial-lateral rotation with respect to the prosthesis frame and also provides energy storage capabilities. The present invention further relates to a prosthetic ankle joint having an adjustable range of medial-lateral rotation about the prosthesis frame.

BACKGROUND OF THE INVENTION

A prosthetic foot must provide stable support to the user under a variety of conditions. Such conditions include a variable stride and a range of different activities. In particular, a prosthetic foot has long been sought that can provide stable support for a user who is walking on an ever changing terrain, such as that encountered in normal daily activity. To achieve this objective, a prosthetic foot would ideally provide a range of motion in a medial-lateral direction. It is also desirable that the prosthetic foot has energy storage capabilities to provide a more normal gait.

Dynamic response prosthetic feet are preferred for active amputees. The energy storage capabilities of the feet give them a spring-like functionality, which improves the feel and overall function of the prostheses. Two widely used types of prosthetic feet are high profile dynamic feet and low profile multiaxial feet.

High profile dynamic feet consist of a long L-shaped piece of material attached to a base plate. The L-shaped piece of material may be alternatively referred to as a frame. Typically, the frame is elastic and therefore provides some energy storage capability. Generally, the frame is a composite, such as a carbon fiber laminate or a polymeric material. At present, all high profile dynamic feet have a rectangular cross section relative to the frame and therefore movement of the footplate is typically limited. Such high profile dynamic feet have advantages because of their high-energy storage capability. High-energy storage occurs in the frame of the prosthesis. High profile dynamic feet have the longest frame, and thus act as the biggest springs and, accordingly, store the most energy. However, high profile dynamic feet also present some drawbacks. Principally, the high profile dynamic feet have no ankle motion and therefore are not capable to conforming to a changing terrain. The foot portion of a high profile dynamic foot stays in the same position relative to the frame regardless of whether the amputee is walking on an incline, walking on uneven terrain or moving in a side-to-side direction.

The multiaxial dynamic feet of the prior art attempt to simulate motion of the ankle and are generally considered more stable than high profile dynamic feet. A disadvantage of the multiaxial dynamic foot is that generally it is a low profile prosthesis. By comparison to the high profile dynamic feet, low profile multiaxial dynamic feet can only store energy in their keel, which is a much smaller frame and, thus, a much smaller spring. Accordingly, there is correspondingly less energy storage. Therefore, with the prior art devices, there presently is a tradeoff between increased stability and improved energy storage capability.

Typically, the multiaxial feet of the prior art possess an axis of rotation through the ankle joint that lies transverse to the normal anterior-posterior alignment of the foot. Subsequently, such multiaxial prosthetic feet, although typically providing a range of rotation in an anterior-posterior direction, have limited freedom to move in a medial-lateral direction. Subsequently, the prior art multiaxial feet typically only allow a small amount of medial-lateral tilt and do not allow true rotation in the medial-lateral direction. Tilt is distinguishable from true rotation in that tilt may occur along any of a multitude of axes, whereas rotation occurs about one axis. Tilt may also be described as wobble. Typically, in the prior art devices, the amount of medial-lateral tilt is a consequence of some looseness in the ankle joint. This looseness is generally accomplished through the use of an elastomeric member in the ankle joint, which member can then compress to a limited degree, thus accommodating medial-lateral tilt. However, it can be difficult to control the tilting motion. Generally, the prior art devices do not possess an axis of rotation through an ankle joint where the axis of rotation lies in the anterior-posterior direction. Furthermore, elastomeric member tends to wear out.

Some of the prior art prosthetic feet provide a range of motion in an anterior-posterior direction. Providing this range of motion is accomplished, for example, by providing a flexible foot that includes an ankle member that flexes in the anterior-posterior direction. Another prior art device provides anterior-posterior motion by using a very high modulus material that permits limited deformation under a high load. This high modulus elastic material is typically positioned between the foot and the frame. As the load on the frame changes during the normal transfer of weight that occurs during walking, the high modulus elastic material flexes to a limited extent. Still another prior device uses an o-ring positioned at the end of the frame where the frame connects to the foot. This o-ring is typically made of a high modulus material and will deform to a limited extent as weight is transferred during a normal stride.

Typical among the devices that rely on a high modulus elastic material for flexibility, the range of motion is necessarily limited. If the material forming at least part of the connection between the frame and the foot has too low a modulus, then control over the foot during normal walking will be compromised. Some of the prior art suggests that a limited degree of medial-lateral movement will occur as a result of the compression of the high modulus elastomeric material positioned between the frame and the foot. Such movement has been described in the art as a slight rocking or a slight tilting motion. The prior art further teaches that although some medial-lateral rocking motion can be accomplished, generally, medial-lateral movement is resisted.

Still another prior art device provides an elastomeric bushing about a heel ankle connector pin. As with the other prior art devices already described, this bushing material is a high modulus elastomer. Accordingly, some compression of the elastomer may take place during the normal weight transfer accompanying walking and result in a small amount of medial-lateral tilt or wobble. As provided above, prostheses that rely on a high modulus elastic material for flexibility tend to have a problem with durability because they wear out with repeated loading and unloading.

Lack of a true hinge allowing rotation in the medial-lateral direction is a disadvantage. True control of movement in a medial-lateral direction about a unitary axis is difficult to achieve in the prior art devices. Any medial-lateral movement in these devices is limited to a tilting movement. This tilting movement can occur along any of an infinite number of axes. Because it is not possible to control every possible axis along which the prior art foot may move, medial-lateral directional control can be difficult to achieve and, therefore, medial-lateral movement is typically constrained. Not surprisingly, the prior art devices limit a full range of medial-lateral movement. For example, in many prior art multiaxial feet, movement of the foot occurs through compression of an elastomeric pad positioned in the ankle region of the foot. Thus in order to provide movement of the foot in a medial-lateral direction the entire elastomeric pad must be of a modulus that affects movement in all directions. In such a multiaxial foot, there is no independent control over movement in a singular direction or line of action.

It would therefore be an advantage to have a prosthetic foot that offered the stability advantages of a multiaxial dynamic foot with the energy storage capabilities of a high profile dynamic foot. It would be an even further advantage to have a prosthetic foot that allows true medial-lateral rotation. It would be at an even further advantage to have an adjustable prosthetic foot that would allow the manufacturer or wearer to select a range of medial-lateral rotation best suited to a wearer's needs.

It would be an even further advantage to have a high profile multiaxial prosthetic foot that could allow free rotation about an axis that lies in the anterior-posterior direction.

SUMMARY OF THE INVENTION

In accordance with the principals of the present invention, there is provided a high profile multiaxial prosthetic foot providing rotation of a footplate in a medial-lateral direction. According to one embodiment, the high profile multiaxial prosthetic foot includes a tubular frame connected to a footplate using a spring connector. In embodiments of the present invention, the spring connector may include a high modulus elastic material, a torsional spring or combinations of these. Thus, the present invention provides a high profile multiaxial prosthetic foot that includes a high profile component and a multiaxial component.

The present invention also provides a high profile multiaxial dynamic prosthetic foot having an adjustable range of medial-lateral rotation. The medial-lateral rotation of the prosthetic foot of the present invention may be adjusted to accommodate the individual needs of the wearer.

The present invention provides a prosthetic foot including: a frame having a first axis and a second axis; a connector connected to the frame, the connector being adapted to rotate about the first axis; and a footplate attached to the connector.

Thus, it will be seen that according to principals of the present invention there is provided a prosthetic foot that provides both the energy storage capabilities of a high profile prosthesis with the stability of a multiaxial prosthesis. The high profile multiaxial prosthetic foot of the present invention provides medial-lateral rotation as compared to the slight medial-lateral tilting or rocking of the prior art devices. In a preferred embodiment, the medial-lateral rotation is controlled about a unitary axis. Furthermore, the high profile multiaxial prosthetic foot of the present invention provides a true hinge in the ankle joint region.

Embodiments of the present invention further provide a high profile multiaxial prosthetic foot having an ankle joint wherein the axis of rotation lies along the longitudinal axis of the foot. The prosthetic foot of the present invention further provides the capability of free rotation about the ankle joint about its axis of rotation.

DESCRIPTION OF THE DRAWINGS

FIG. 4 is an end view of one embodiment of a frame/connector/footplate assembly made in accordance with the principles of the present invention.

FIG. 5 is an end view of an alternative embodiment of a frame/connector/footplate assembly made in accordance with the principles of the present invention.

FIG. 6 is another embodiment of a frame/connector/footplate assembly made in accordance with the principles of the present invention.

FIG. 7 is an end cross-sectional view of another embodiment of a high profile multiaxial prosthetic foot made in accordance with the principles of the present invention.

FIG. 8 is an end cross-sectional view of the high profile multiaxial prosthetic foot made in accordance with the principles of the present invention illustrating means for rotation control.

FIG. 14a is a side view of a high profile multiaxial prosthetic foot made in accordance with the principles of the present invention showing an adjustable displacement of a frame with respect to the foot.

FIG. 14b is a side view of a high profile multiaxial prosthetic foot made in accordance with the principles of the present invention showing an adjustable displacement of a frame with respect to the foot.

FIG. 15 is an end view of a high profile multiaxial prosthetic foot made in accordance with the principles of the present invention showing the displacement of a frame with respect to the vertical alignment of a residual limb.

DETAILED DESCRIPTION OF THE INVENTION

Figure 1:
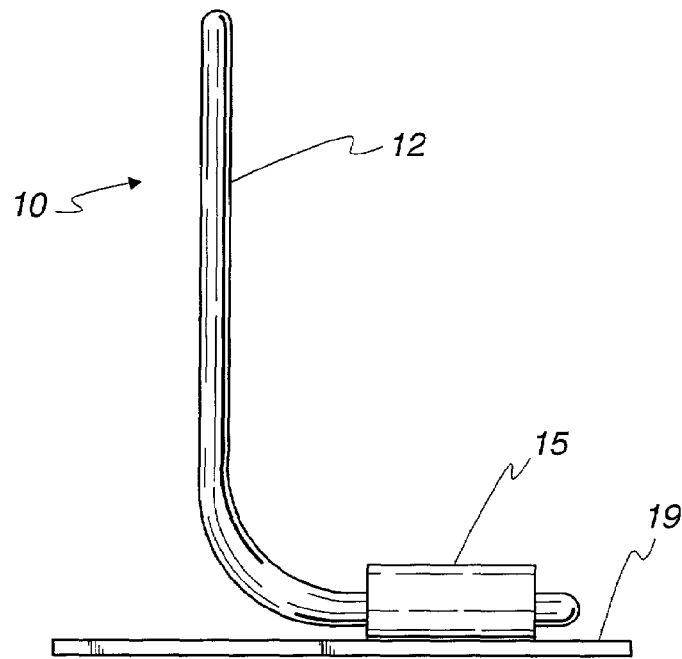
FIG. 1 is a side view of an embodiment of the high profile multiaxial prosthetic foot made in accordance with the principles of the present invention.
Figure 2:
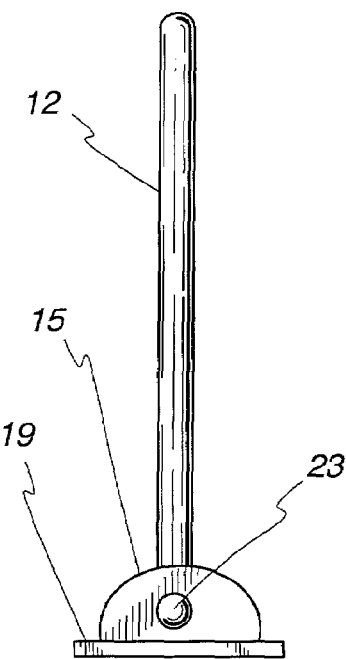
FIG. 2 is a schematic showing an end view of the high profile multiaxial prosthetic foot of FIG. 1.

In FIG. 1, a high profile multiaxial prosthetic foot ("prosthetic foot") made in accordance with the principles of the present invention is labeled 10. The prosthetic foot 10 includes a frame 12, a connector 15 and a footplate 19. An upper portion of the frame 12 may be connected to socket (not shown) that is connected to a leg of the human wearer of the prosthetic foot 10 and a lower portion of the frame 12 is adapted to connect to the footplate 19. In a preferred embodiment, the frame 12 has a generally circular cross-section. Of course, other suitable cross-sections may be used. The connector 15 is adapted to allow rotation of the frame 12 about an axis that is aligned with the longitudinal axis of the footplate 19. As shown in FIG. 2, an ankle joint 23 defines the connection between the frame 12 and the connector 15. The footplate 19 is attached to the connector 15, and, preferably, the footplate 19 is rigidly attached to the connector 15. Thus, it can be seen that the footplate 19 is free to rotate about an axis defined by the ankle joint 23, the axis of rotation lying along the longitudinal axis of the footplate 19 and the lower portion of the frame 12. The prosthetic foot 10 may also be adapted for anterior-posterior movement, by, for example, providing means for the elastic deformation of the connector 15, the frame 12, and/or the footplate 19. Thus, the prosthetic foot 10 may provide multiaxial movement.

The frame may be constructed of a high strength polymer or a composite material such as a carbon fiber laminate, for example. In a preferred embodiment, the frame is an L-shaped member. Being a generally L-shaped member, the frame defines a first axis and a second axis. The footplate may also be constructed of a high strength polymer or a composite material such as a carbon fiber laminate.

Figure 3:
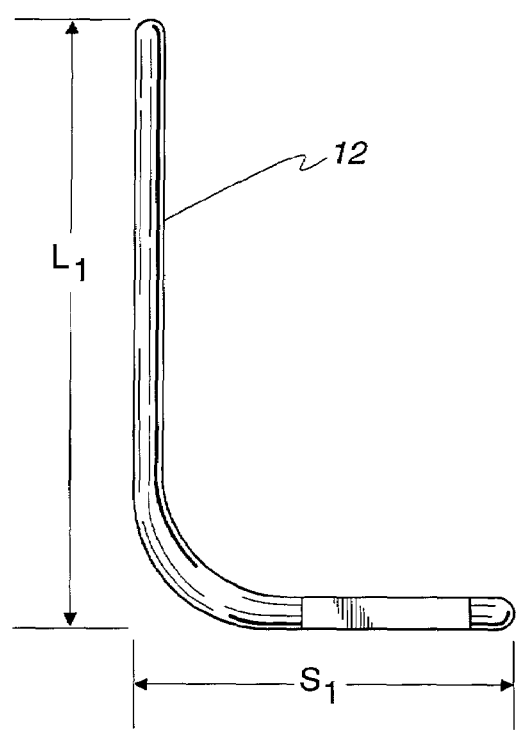
FIG. 3 is a side view of the frame of FIG. 1.

In FIG. 3, the frame 12 is depicted removed from the connector 15. The frame 12 may be described as having a generally long axis L1 along the upper portion of the frame 12 and a generally short axis S1 along the lower portion of the frame 12, however, long axis L1 and short axis S1 may be of any length as required by a wearer of the prosthetic foot 10. The short axis S1 is connected to the connector 15 through the ankle joint 23. In one embodiment, when the prosthetic foot 10 is assembled, the short axis S1 is aligned with the longitudinal axis of the footplate 19.

FIGS. 4, 5 and 6 show alternative embodiments of the present invention and more particularly, show alternative means for connecting a frame to a footplate. In FIG. 4, a frame 42 is connected to a connector 45 through an ankle joint 43. The connector 45 may be any general shape so long as it does not preclude the utility of the prosthetic foot 10. The connector 45 is generally configured so that it may provide an ankle joint 43 having an axis of rotation that lies along an anterior-posterior direction. The connector 45 is attached to the footplate 49. In this embodiment, the connector 45 is adapted to frictionally receive the frame 42. Thus, medial-lateral rotation of the frame 42 about its short axis is limited by the coefficient of friction existing between the connector 45 and the frame 42 at the ankle joint 43. The connector 45 may be made of any suitable material that preserves the functionally of the prosthetic foot 10. For example, a high strength polymer, a carbon fiber laminate or a high modulus elastomeric material may be used for the connector 45. A high modulus elastomeric material, for example, may allow movement of the footplate 49 in an anterior-posterior direction via compression of the connector 45.

In FIG. 5, an alternative embodiment of the connector of the present invention is illustrated. Frame 52 is connected to a spring 55 through an ankle joint 53. Spring 55 is then attached to a footplate 59. In the embodiment depicted in FIG. 5, connector 55 is in the form of a torsional spring. However, other spring designs, such as a leaf spring, may be used. The spring 55 is generally configured so that it may provide an ankle joint 43 having an axis of rotation that lies along an anterior-posterior direction. The spring 55 may be constructed of a carbon fiber laminate or metal, for example. Thus, the amount of rotation of the footplate 59 about the ankle joint 53 may be limited by the spring constant for the spring 55. In this embodiment, it is preferred that the frame 52 be fixedly attached to the spring 55 at the ankle joint 53. However, it may possible to allow rotation of the short axis of the frame 52 within the ankle joint 53 with respect to the spring 55, by providing that the spring 55 is adapted to frictionally receive the frame 52. Thus, the amount of rotation of the footplate 59 about the ankle joint 53 is limited both by the coefficient of friction existing between the short axis of the frame 52 and the spring 55 at the ankle joint 53 and also the spring constant of the spring 55.

In FIG. 6, yet another embodiment of a frame/connector/footplate assembly made in accordance with the principles of the present invention illustrated. In FIG. 6, a frame 62 is connected to a spring 65 at an ankle joint 63. In the embodiment depicted in FIG. 6, spring 65 is in the form of a torsional spring. However, other spring designs, such as a leaf spring, may be used. The spring 65 is generally configured so that it may provide an ankle joint 63 having an axis of rotation that lies along the short axis of the frame 62. The spring 65 may be constructed of a carbon fiber laminate or metal, for example. Thus, the amount of rotation of the footplate 69 about the ankle joint 63 may be limited by the spring constant for the spring 65. In this embodiment, a connector 64 is also used. The spring 65 and the connector 64 are both attached to the footplate 69. Rotation of the frame 62 within the ankle joint 63 may be constrained by providing that the spring 65 is adapted to frictionally receive the frame 62. Rotation of the frame 62 within the connector 64 may be constrained by providing that the connector 64 is adapted to frictionally receive the frame 62. The rotation of the footplate 69 may be limited by the coefficient of friction between the frame 62 and the spring 65, the coefficient of friction between the frame 62 and the connector 64, or the spring constant of the spring 65, or combinations thereof.

In FIG. 7, a cross-sectional end view of a high profile multiaxial prosthetic foot 70 is shown. In this embodiment, the frame 72 is connected to a spring 74 by a setscrew 73. The setscrew 73 may fixedly attach the spring 74 to the frame 72 and limit or even prevent the rotation of the frame 72 within the spring 74. A connector 75 is adapted to rotationally receive the frame 72. The connector 75 is attached to the footplate 79. The spring 74 may abut the footplate 79.

In FIG. 8, a cross-sectional end view of another embodiment of a prosthetic foot of the present invention is shown. In this embodiment, a control element 81 is adapted to receive a frame 82. Rotation stop 87, 88 extend from control element 81. Also shown are a connector 85 and a footplate 89. The rotation of the footplate 89 about its axis is limited by the rotation stop 87, 88. The footplate 89 may rotate either clockwise or counter-clockwise until reaching the rotation stop 87, 88. It will be recognized that there are other adaptations of the rotation adjustment means provided by the rotation stop 87, 88 and the control element 81. The structure of the rotation stop 87, 88 and the control element 81, and the related function of rotation control, are further described below with respect to FIG. 9.

Figure 9:
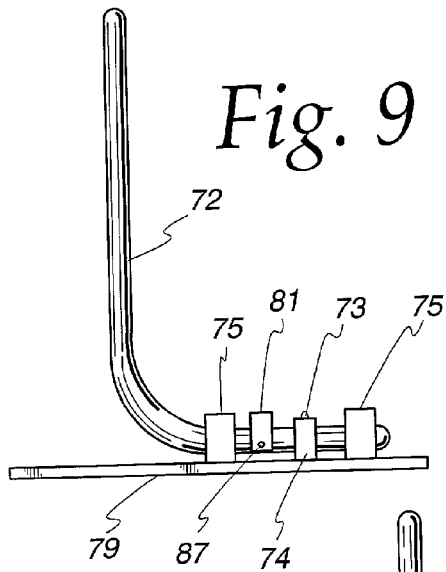
FIG. 9 is an embodiment of a high profile multiaxial prosthetic foot made in accordance with the principles of the present invention showing alternate connector means and means for rotation control.

In FIG. 9, a side-view of a prosthetic foot incorporating a connector 75, a spring 74 and a control element 81. The frame 72 is connected to a spring 74 by a setscrew 73. The connector 75 is adapted to rotationally receive the frame 72. The connector 75 is also attached to the footplate 79 in a known manner. The spring 74 may abut the footplate 79. The control element 81 is adapted to receive the frame 72. In the preferred embodiment, the control element 81 is rigidly attached to the frame 72. The control element includes a rotation stop 87. The rotation of the footplate 89 about its axis is limited by the rotation stop 87. A second rotation stop may be included as described above. The footplate 89 may rotate either clockwise or counter-clockwise until reaching a rotation stop.

Figure 10:
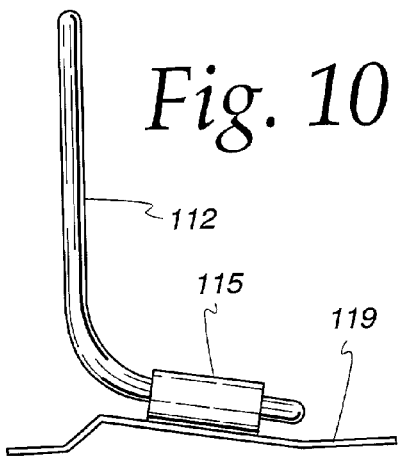
FIG. 10 is a side view of still another embodiment of a high profile multiaxial prosthetic foot made in accordance with the principles of the present invention.

In FIG. 10, yet another embodiment of a prosthetic foot of the present invention is illustrated. In this embodiment, a frame 112 is connected to a connector 115, which in turn is attached to a footplate 119. In this embodiment, the footplate 119 is formed to allow the use of a frame 112 wherein the angle between the short axis and the long axis of the frame 112 is greater than 90°.

Figure 11:
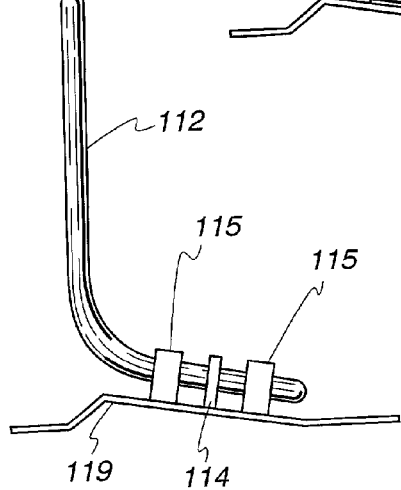
FIG. 11 is a side view of still another embodiment of a high profile multiaxial prosthetic foot made in accordance with the principles of the present invention.

In FIG. 11, yet another embodiment of a prosthetic foot of the present invention is illustrated. In this embodiment, a frame 112 is rotatably connected to a connector 115, which in turn is fixedly attached to a footplate 119. The frame 112 is connected to a spring 114. The spring 114 may abut the footplate 119. In this embodiment, the footplate 119 is formed to allow the use of a frame 112 wherein the angle between the short axis and the long axis of the frame 112 is greater than 90°.

Figure 12:
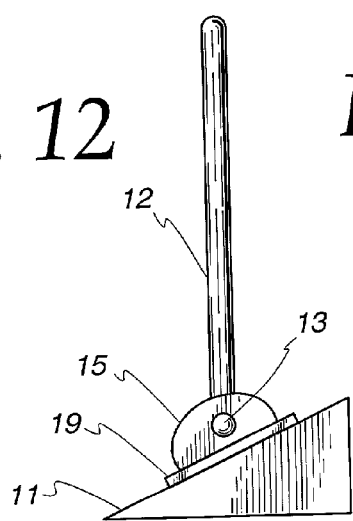
FIG. 12 is an end view of a high profile multiaxial prosthetic foot made in accordance with the principles of the present invention showing rotation of the prosthetic foot about an axis aligned with the longitudinal axis of the foot.

FIG. 12 illustrates the ability of a prosthetic foot made in accordance with the principles of the present invention to provide medial-lateral rotation. In FIG. 12, an end view of the prosthetic foot 10 is shown. As described in the previous embodiments, a frame 12 is connected to a connector 15 at an ankle joint 13 with the connector 15 being attached to a footplate 19. In FIG. 12, the prosthetic foot is positioned on an inclined plane 11. This is analogous to a wearer of a prosthetic foot standing sideways on a hill. Thus, the longitudinal axis of the footplate 19 is transverse to the direction of incline of the incline plane 11. It can be seen that the high profile multiaxial prosthetic foot of the present invention allows rotation in a medial-lateral direction, thus, stabilizing the footplate 19 in such a position.

Figure 13:
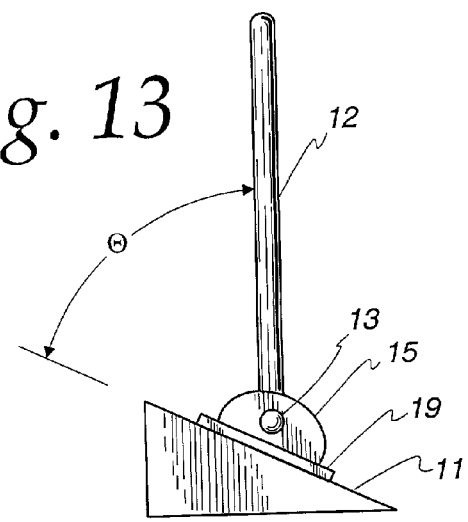
FIG. 13 is an end view of a high profile multiaxial prosthetic foot made in accordance with the principles of the present invention showing rotation of the prosthetic foot about an axis aligned with the longitudinal axis of the foot.

FIG. 13 likewise illustrates an embodiment of a prosthetic foot of the present invention positioned on an inclined plane 11. In FIG. 13, there is further defined an angle θ. The angle θ is the angle formed between the plane of the incline and the long axis of the frame 12. Because of the orientation of the ankle joint 13, θ may effectively vary between 0 and 180°.

The prosthetic foot of the present invention may be adapted to provide adjustment of a frame with respect to a connector and a footplate. In FIG. 14a and FIG. 14b, for example, a frame 112 is shown connected to a connector 115. The connector 115 is attached to a footplate 119. One end of the footplate 119 defines an imaginary vertical line v. A distance $x_1$ is defined by the separation distance between v and the long axis of the frame 112. By positioning the long axis of the frame 112 closer to the connector 115 a second distance $x_2$ may be defined between v and the long axis of the frame 112. The distance $x_1$ is less than the distance $x_2$. Thus, the position of the long axis of the frame 112 may be adjusted with respect to the connector 115 and the footplate 119. Along its longitudinal axis, the footplate 119 defines a first end and a second end. Thus the position of the long axis of the frame 112 may be adjustably located with respect to the first end or the second end of the footplate 119. The adjustable positioning of the frame 112 with respect to the footplate 119 may accomplished, for example, by adjustably connecting the frame 112 to the connector 115. Thus, the short axis of the frame 112 may be moved to a desired position along the longitudinal axis of the footplate 119 and then fixed in position by the connector 115 with respect to further movement along the longitudinal axis of the footplate. Referring to FIG. 7, in one embodiment for example, the frame 72 may be adjustably positioned with respect to the footplate 79 as described above and this position fixed by tightening setscrew 73.

In FIG. 15, for example, a frame 112 is shown connected to a connector 115. The connector 115 is attached to a footplate 119. Further illustrated is a residual limb 120. As known in the art, the residual limb is attached to a socket that is attached to the frame 112. The residual limb 120 defines a generally vertical axis $v_1$. An angle $\theta_1$ is defined by the long axis of the frame 112 and $v_1$. Thus it can be seen that $\theta_1$ may be varied to allow the residual limb 120 to be offset with respect to the footplate 119. The footplate 119 can be seen to also define a top plane and a bottom plane. As illustrated in FIG. 15, the connector 115 is attached to the footplate 119 at the top plane of the footplate 119. Thus, the long axis of the frame 112 may be adjustably positioned with respect to the top plane so that the long axis defines an angle with respect to the top plane that is different than 90°. Referring to FIG. 7, in one embodiment for example, the frame 72 may be adjustably positioned with respect to the footplate 79 as described above and this position fixed by tightening setscrew 73.

As is known in the art, the footplate of the prosthetic foot of the present invention may be covered with an anthropomorphic flexible polymer in the shape of a foot.

The high profile multiaxial prosthetic foot made in accordance with the principles of the present invention allows free rotation of a prosthetic footplate about an axis that lies along the longitudinal axis of the footplate. Thus, such a prosthetic foot provides free rotation from 0 to 180° in a medial-lateral direction. A high profile multiaxial prosthetic foot made in accordance with the principles of the present invention further provides means to control the amount of rotation of the footplate. Thus, the present invention provides a high profile multiaxial prosthetic foot that allows true medial-lateral rotation as opposed to mere medial-lateral tilt.

There has been provided in accordance with the present invention, a high profile multiaxial prosthetic foot providing stability for the user in conditions requiring medial-lateral rotation. While the invention has been described with specific embodiments, many alternatives, modifications and variations will be apparent to those skilled in the art in light of the forgoing description. Accordingly, it is intended to include all such alternatives, modifications and variations set forth within the spirit and scope of the appended claims.

What is claimed is:

1. A prosthetic foot comprising:
    an L-shaped frame having a first axis and a second axis, the first axis forming a substantially horizontal leg of the L-shaped frame;
    a rigid connector connected to the frame, the connector defining an opening through itself which receives the horizontal leg in a direction substantially along the first axis so that the connector is rotatable about the substantially horizontal leg; and
    a footplate attached to the connector, the footplate defining a first end and a top plane such that the footplate is also adapted to rotate about the substantially horizontal leg in unison with the connector and flex with respect to the second axis.

2. The prosthetic foot of claim 1 wherein the frame is a tubular L-shaped member.

3. The prosthetic foot of claim 1 wherein the frame is manufactured from a material, the material selected from the group consisting of high strength polymer and composite material.

4. The prosthetic foot of claim 1 wherein the connector is manufactured from a material, the material selected from the group consisting of a high modulus elastomeric material, a high strength polymer and a composite material.

5. The prosthetic foot of claim 1 wherein the second axis of the frame is adjustably positioned with respect to the first end of the footplate.

6. The prosthetic foot of claim 1 wherein the second axis of the frame is adjustably positioned with respect to the top plane of the footplate.

* * * * *